(12) United States Patent
Yang

(10) Patent No.: US 8,213,702 B2
(45) Date of Patent: Jul. 3, 2012

(54) AUTOMATED TESTING DEVICE FOR FASTENER

(76) Inventor: Yea-Yih Yang, Hsinchu Hsien (TW)

( * ) Notice: Subject to any disclaimer, the term of this patent is extended or adjusted under 35 U.S.C. 154(b) by 434 days.

(21) Appl. No.: 12/432,760

(22) Filed: Apr. 30, 2009

(65) Prior Publication Data
US 2010/0278417 A1  Nov. 4, 2010

(51) Int. Cl.
*G06K 9/00* (2006.01)
(52) U.S. Cl. ........................................ 382/141
(58) Field of Classification Search ............ 382/141, 382/152
See application file for complete search history.

(56) References Cited

U.S. PATENT DOCUMENTS

| | | | |
|---|---|---|---|
| 4,823,396 A * | 4/1989 | Thompson | 382/152 |
| 4,828,100 A * | 5/1989 | Hoppmann et al. | 198/392 |
| 5,164,995 A * | 11/1992 | Brooks et al. | 382/152 |
| 5,661,249 A * | 8/1997 | Rupp et al. | 73/865.8 |
| 6,259,960 B1 * | 7/2001 | Inokuchi | 700/110 |
| 6,480,002 B1 * | 11/2002 | Jung et al. | 324/425 |
| 7,164,783 B2 * | 1/2007 | Yang et al. | 382/152 |
| 7,245,759 B2 * | 7/2007 | Jones et al. | 382/152 |
| 7,343,034 B2 * | 3/2008 | Jones et al. | 382/152 |
| 7,364,043 B2 * | 4/2008 | Ong et al. | 209/652 |
| 7,679,758 B2 * | 3/2010 | Wei et al. | 356/625 |

* cited by examiner

*Primary Examiner* — Michael A Lyons
(74) *Attorney, Agent, or Firm* — Leong C. Lei

(57) ABSTRACT

The automated testing device contains a platform, a rotational plate on a top side of the platform, and, around the rotational plate and along a rotating direction of the rotational plate, an uploading member, a guiding member, an optical testing member, and an unloading member are provided and located in this sequence. The uploading member places fasteners in an upright manner on the top side of the rotational plate. The guiding member aligns the upright fasteners along a specific path. The optical testing member obtains and examines at least a profile image of each fastener. The unloading member screens out substandard fasteners and collects those qualified fasteners out of the rotational plate.

6 Claims, 7 Drawing Sheets

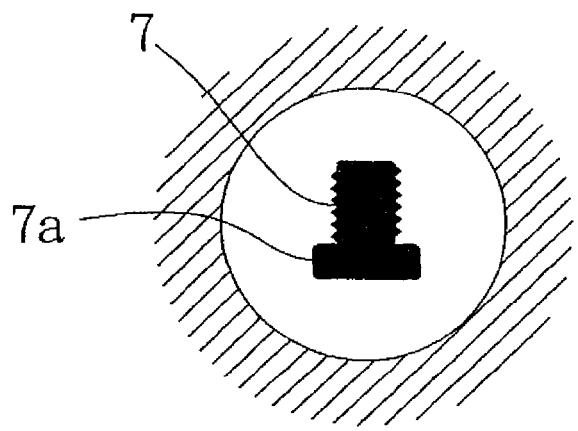
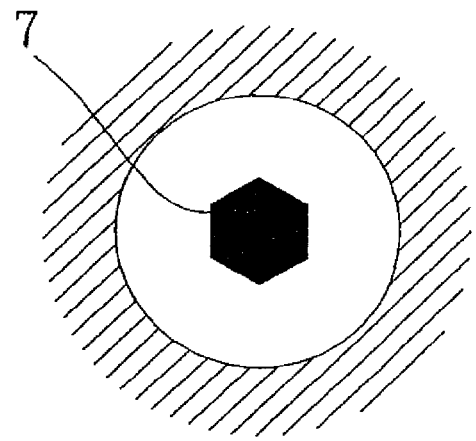
FIG.3  FIG. 4
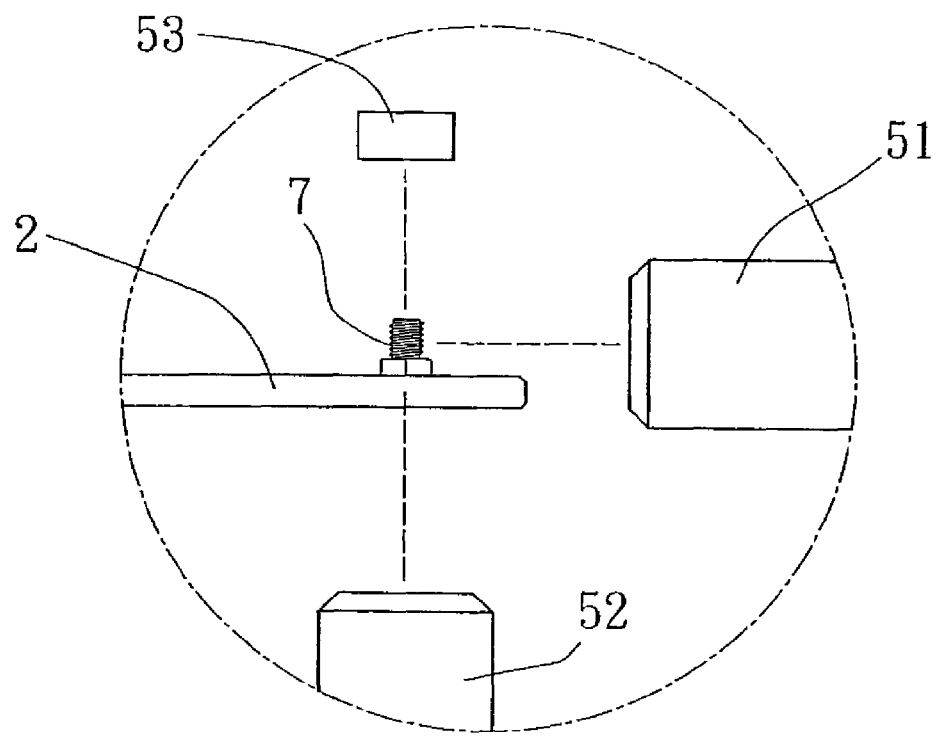
FIG. 5

AUTOMATED TESTING DEVICE FOR FASTENER

TECHNICAL FIELD OF THE INVENTION

The present invention generally relates to testing devices for fasteners such as bolts, screws, rivets, etc., and more particularly to a testing device automatically screening out substandard fasteners by obtaining and examining their optical images.

DESCRIPTION OF THE PRIOR ART

As consumer appliances are getting smaller, lighter, thinner, and shorter, fasteners such as bolts, screws, rivets, etc., used by these appliances are also getting smaller and having various different specifications. Non-compliant fasteners not only could not function properly but even could damage the products they are applied to. Therefore, testing and screening the fasteners after they are produced or before they are applied is important and necessary, especially for high-priced products or for manufacturers of automated assembly lines.

A conventional testing device for fasteners has a rotational platform with a number of slots spaced around the circumference of the platform. Each slot holds a fastener upright. Then, by rotating the platform, the fasteners held in the slots are sequentially moved through a tester which captures the image of each fastener moved through for examination. There are a number of disadvantages for this approach. First, fasteners that could not be held uptight by the slots could be tested. In addition, a large number of platforms have to be prepared for fasteners of various specifications, which is both costly and laborious for switching platforms when changing fasteners.

Another conventional approach is to run two belts in parallel and the fasteners are spaced and clamped between the two belts. The fasteners are then moved by the belts in sequence through the tester. By adjusting the distance between the belts, the approach could be applied to the testing of fasteners of various sizes. However, still some fasteners could not be handled as such and, in order to get a complete profile image of the fasteners, the belts are usually made to be quite thin and therefore more prone to be deformed and broken.

SUMMARY OF THE INVENTION

Even though fasteners have various specifications and sizes, most of the fasteners have a cap section and they can be held in an upright manner with the cap section at the bottom. A major objective of the present invention is therefore to provide an automated testing device for screening fasteners capable of being held this upright manner with high efficiency and accuracy.

To achieve this objective, the automated testing device contains a platform, a rotational plate on a top side of the platform, and, around the rotational plate and along a rotating direction of the rotational plate, an uploading member, a guiding member, an optical testing member, and an unloading member are provided and located in this sequence. The uploading member places fasteners in an upright manner on the top side of the rotational plate. The guiding member aligns the upright fasteners along a specific path. The optical testing member obtains and examines at least a profile image of each fastener. The unloading member screens out substandard fasteners and collects those qualified fasteners out of the rotational plate.

The rotational plate could be made of a metallic material or of transparent glass. When the rotational plate is made of transparent glass, an image capturing element could be positioned beneath the rotational plate to take a bottom-view image of each fastener moving across. The image capturing elements of the optical testing member could be arranged in various viewing angles in accordance with the fasteners to be tested and are not limited to lateral and vertical viewing angles only.

The uploading member could further contain an overturning element between a rail and the top side of the rotational plate. Therefore, for fasteners placed in the rail with their cap sections at the top, they are turned upside down by the overturning element so that they could stand reliably on their cap sections as they are moved on the rotational plate.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIG. 3 is a schematic diagram showing a profile image obtained by an image capturing element of the automated testing device of FIG. 1.

FIG. 4 is a schematic diagram showing a bottom-view image obtained by an image capturing element of the automated testing device of FIG. 1.

FIG. 5 is a schematic diagram showing the positional relationship between a sensor, two image capturing elements, and a fastener under test of the automated testing device of FIG. 1.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
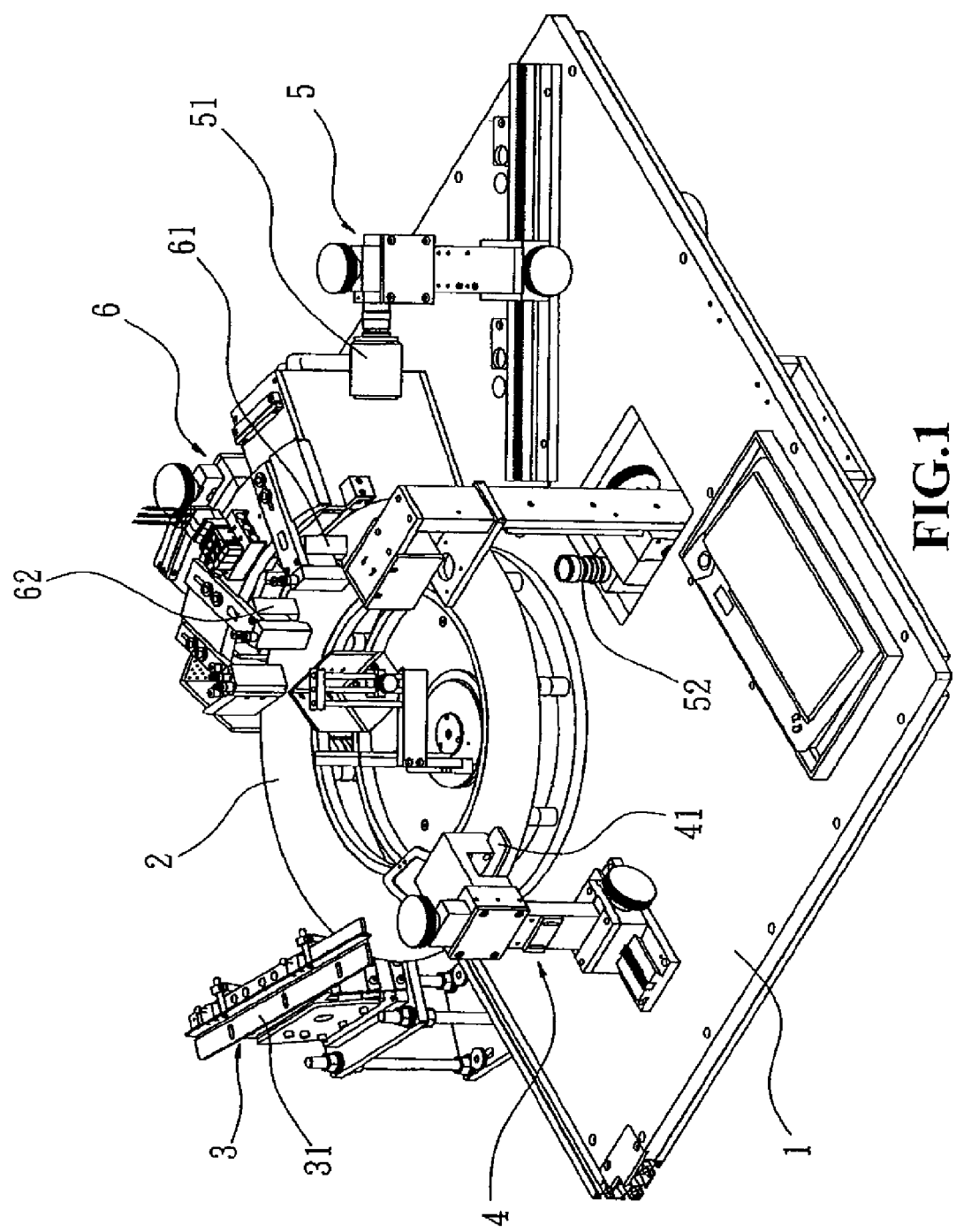
FIG. 1 is a perspective diagram showing an automated testing device according to an embodiment of the present invention.

As shown in FIG. 1, an embodiment of the automated testing device contains a platform 1 and a rotational plate 2 on a top side of the platform 1. Then, around the rotational plate 2 and along a rotating direction of the rotational plate 2, an uploading member 3, a guiding member 4, an optical testing member 5, and an unloading member 6 are provided and located in this sequence.

The rotational plate 2 is circular and could be made of a metallic material or of glass for supporting the fasteners to be tested on a top side around its circumference and moving the fasteners laterally along a rotational direction. When the rotational plate 2 is made of transparent glass, an image capturing element 52 could be positioned beneath the rotational plate 2 to take bottom-view images of the fasteners moving across.

As shown in FIG. 1, the uploading member 3 mainly contains a rail 31 having an output end above the rotational plate 2. The fasteners 7 to be tested are positioned in the rail 31 and supplied sequentially in an upright manner onto the top side of the rotational plate 2 from the output end.

Figure 2:
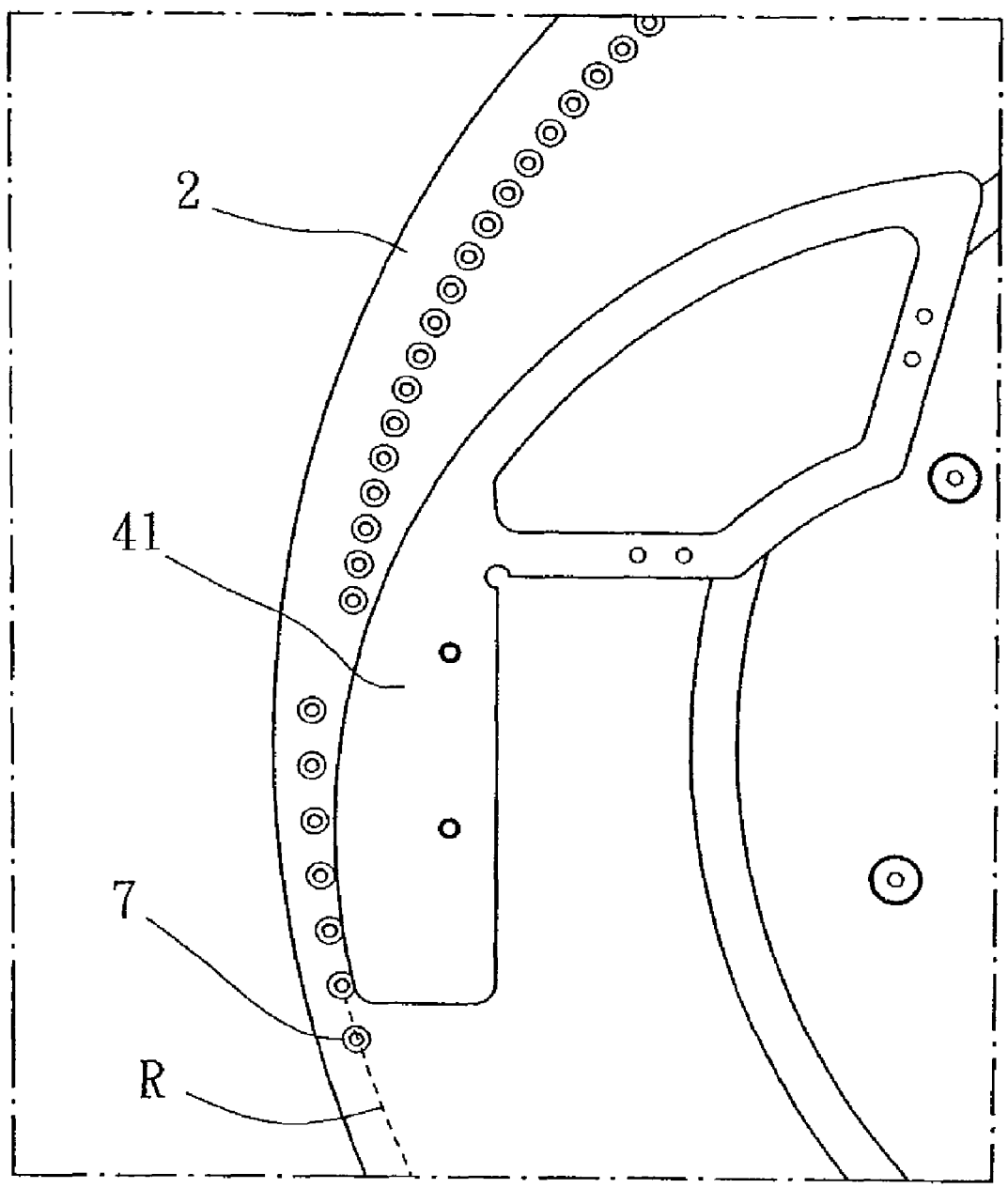
FIG. 2 is a top-view diagram showing the to-be-tested fasteners aligned along a path by a guiding member of automated testing device of FIG. 1.

As shown in FIG. 2, the guiding member 4 has a shunt element 41 such as a fixed curved wall above the rotational plate 2. The fasteners 7 landed on and moved by the rotational plate 2 would be directed by the curved wall of the shunt element 41 to align along a path R.

As shown in FIGS. 1 and 5, the optical testing member 5 contains at least an image capturing element (e.g., a camera) for taking at least a profile image of each fastener moved along the path R for examination. In the present embodiment, a lateral image capturing element 51 and a perpendicular image capturing element 52 are provided for obtaining a profile image (as shown in FIG. 3) and a bottom-view image (as shown in FIG. 4), respectively, of each fastener 7. Please note that the image capturing elements 51 and 52 are positioned such that, when a fastener 7 is moved through a specific location along the path R, it is in focus by the image capturing elements 51 and 52. A sensor 53 is provided above the rotational plate 2 to trigger the image capturing elements 51 and 52 when a fastener 7 is moved through the specific location and detected by the sensor 53. Please note that the image capturing elements 51 and 52 are not limited only to lateral and vertical viewing angles. The images obtained by the image capturing elements 51 and 52 are then processed by a programmable logic controller (PLC) or a computational processing unit (CPU) to conduct automatic analysis and comparison for specification compliance or quality control. During the analysis and comparison, the image and testing result of each fastener 7 could be shown on a display (not shown in the drawings) for an operator to review. Please note that the positions of the perpendicular image capturing element 52 and the sensor 53 could be switched.

Figure 7:
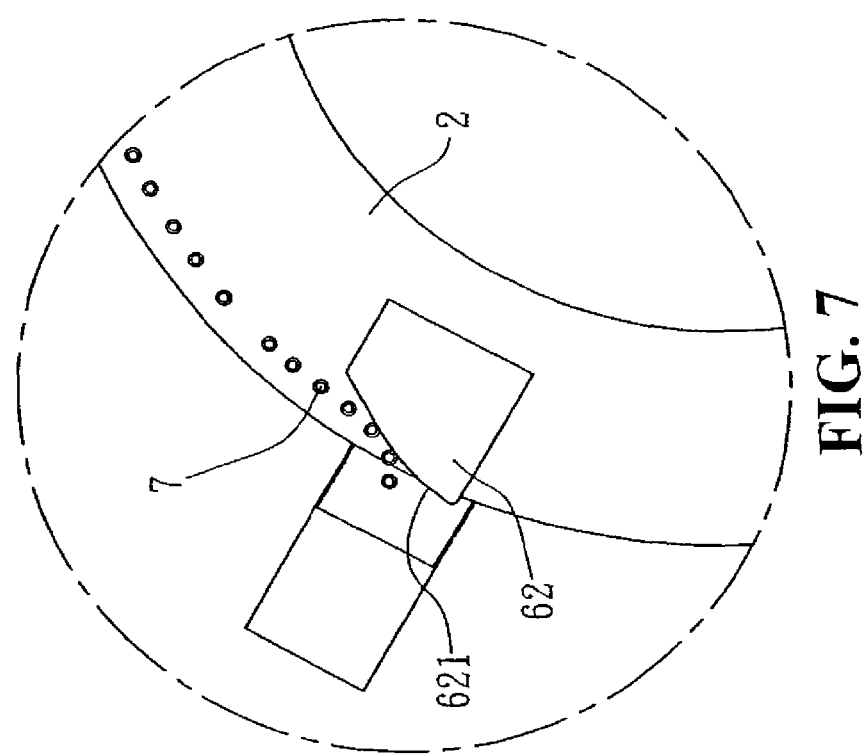
FIG. 7 is a top-view diagram showing qualified fasteners being collected by a second unloader of the automated testing device of FIG. 1.
Figure 6:
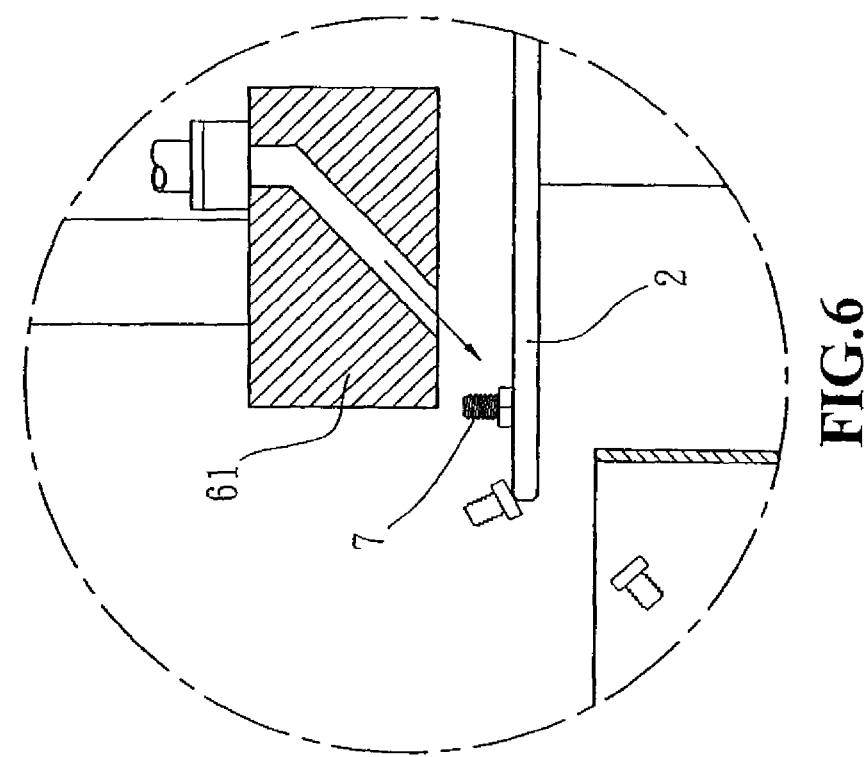
FIG. 6 is a profile diagram showing substandard fasteners being screened out by a first unloader of the automated testing device of FIG. 1.

As shown in FIGS. 1, 6, and 7, the unloading member 6 contains a first unloader 61 and a second unloader 62, both positioned above the rotational plate 2 sequentially in this order along the rotational direction of the rotational plate 2. In the present embodiment, the first unloader 61, engaged by the PLC or CPU, selectively provides a centrifugal (from the rotational plate 2) airflow to knock unqualified fasteners 7 off the rotational plate 2 and into a container. The remaining, qualified fasteners 7 then run into a curved wall 621 of the second unloader 62 and, following the curved wall 621, fall off the rotational plate 2 into another container.

Figure 8:
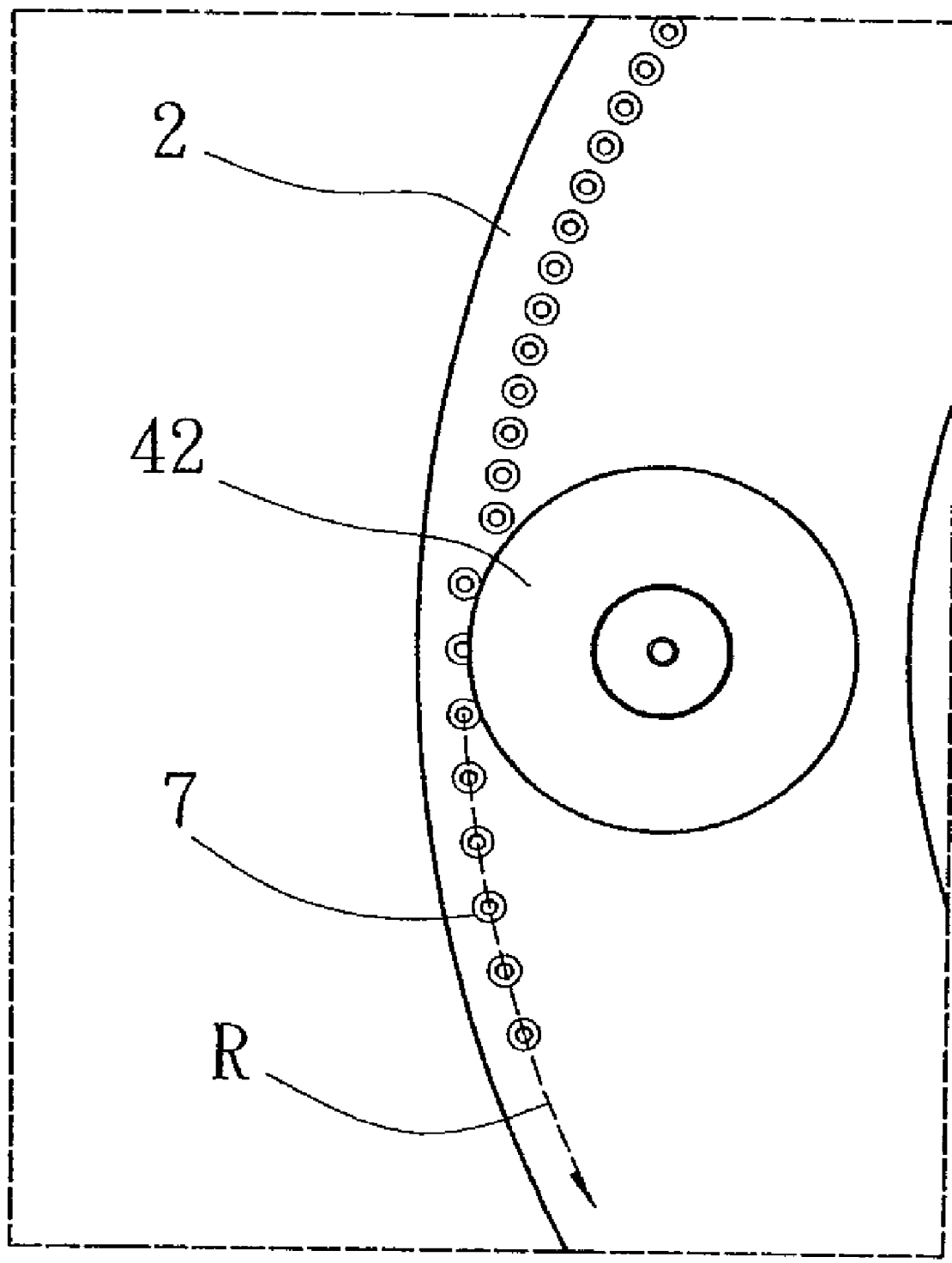
FIG. 8 is a top-view diagram showing an alternative embodiment of a shunt element of the automated testing device of FIG. 1.

In the present embodiment, the shunt element 41 of the guiding member 4 is a curved wall. Alternatively, as shown in FIG. 8, the shunt element 41 is embodied in a motor-driven wheel 42 so that passing-by fasteners 7 are guided and spaced with less friction. This is especially helpful to prevent long fasteners 7 from being tipped off by the shunt element 41.

Figure 9:
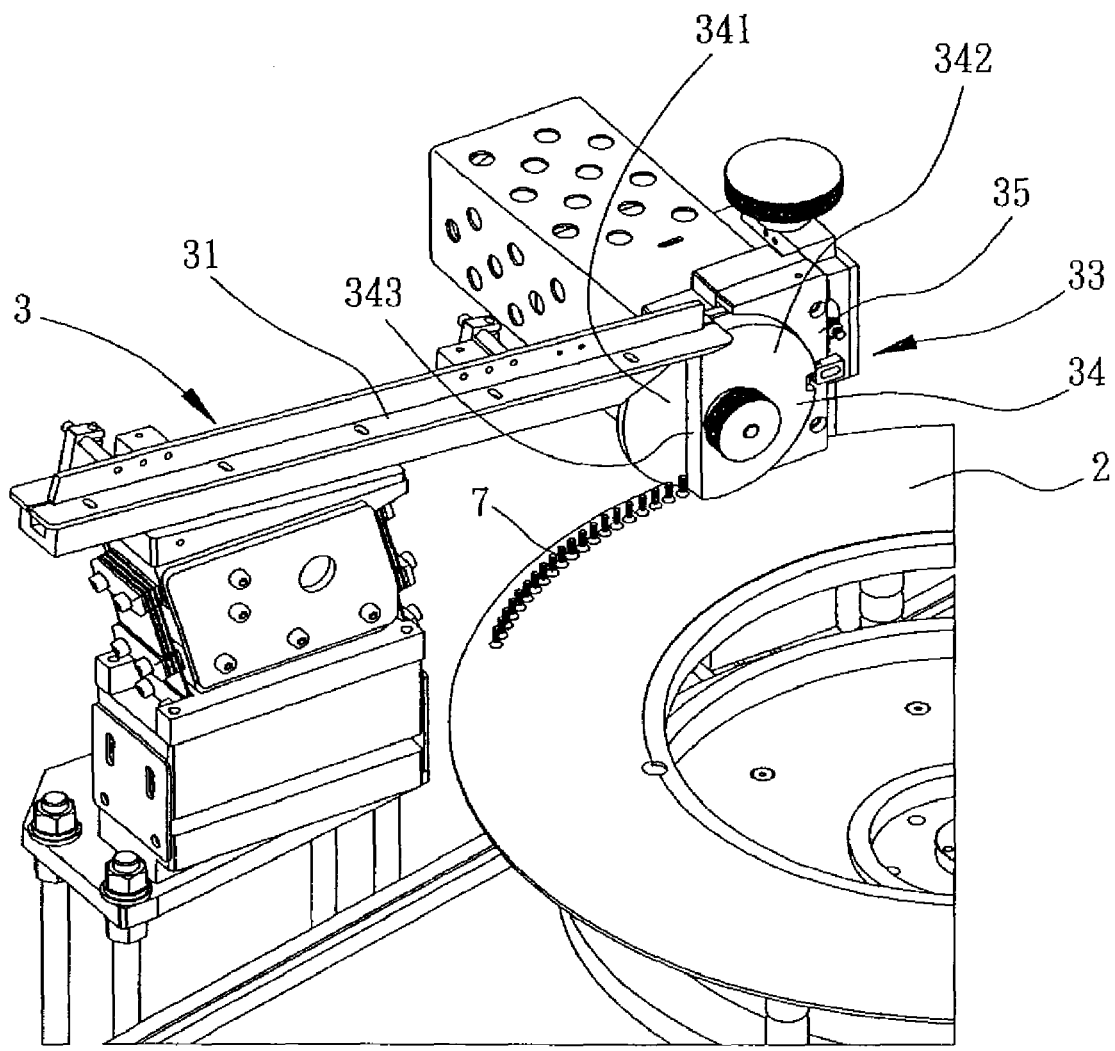
FIG. 9 is a perspective diagram showing an alternative embodiment of an uploading member of the automated testing device of FIG. 1.
Figure 10:
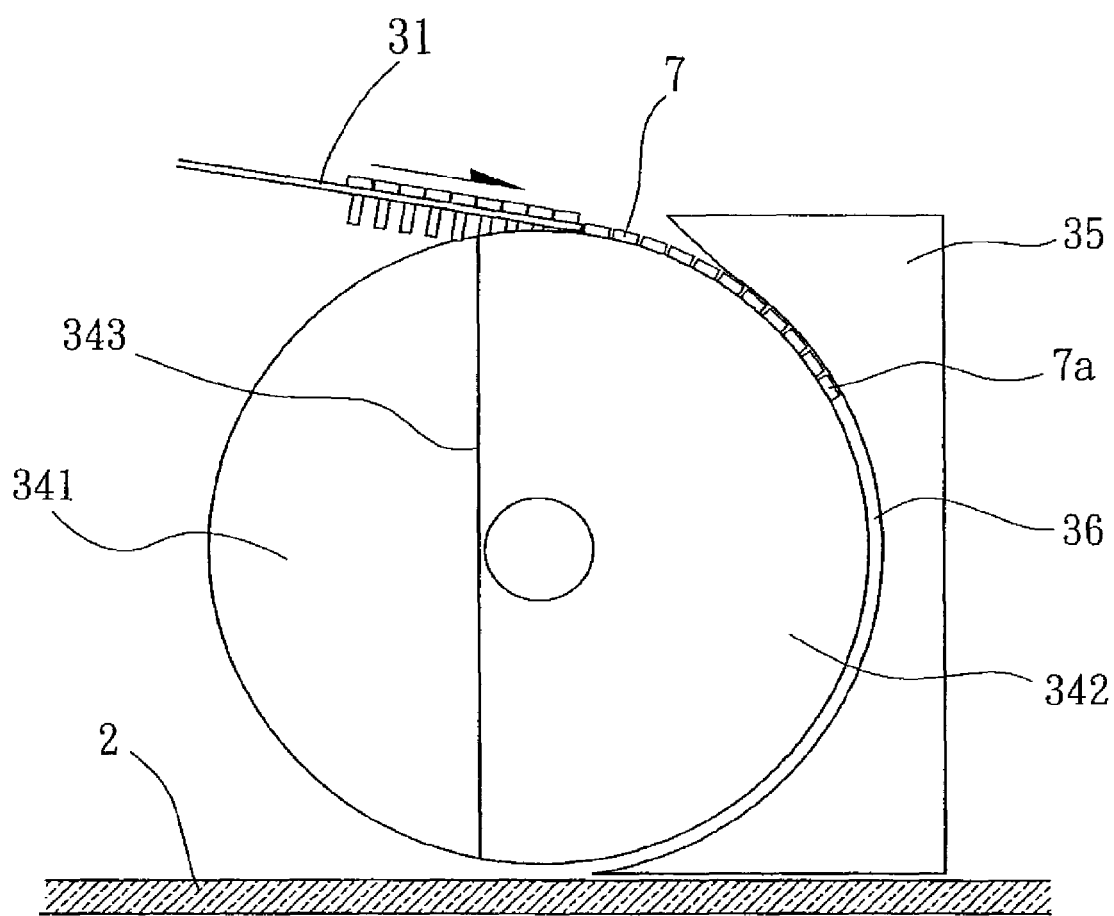
FIG. 10 is a profile diagram showing fasteners are overturned by the uploading member of FIG. 9.

As shown in FIGS. 9 and 10, the uploading member 3 could further contain an overturning element 33 positioned between the output end of the rail 31 and the top side of the rotational plate 2. The overturning element 33 contains a wheel set 34 beneath the rail 31 and the rail 31 is substantially tangential to the wheel set 34. A front portion of the wheel set 34 is matched by a horseshoe-like piece 35 so that a curved passageway 36 allowing a cap section 7a (see also FIG. 3) of the fasteners 7 to move through is formed therebetween. The wheel set 34 contains two wheels 341 and 342 in parallel with a gap therebetween capable of receiving a body section of the fasteners 7. As such, if the uploading member 3 has the fasteners 7 delivered in a cap-on-top manner, the fasteners 7 are first landed between the wheels 341 and 342, and moved by the wheels 341 and 342 through the passageway 36. When the fasteners 7 have become upside down (i.e., cap section 7a is beneath the body section), they are landed reliably on the rotational plate 2.

The wheels 341 and 342 could be motor-driven or not motor-driven. For the former, the wheels 341 and 342 could be driven to turn simultaneously, or only the outer wheel 341 (i.e., the wheel farther away from the center of the rotational plate 2) is driven by the motor. In this embodiment, the inner wheel 342 has a back segment removed so as to form a vertical chord 343 adjacent to the center of the wheel 341. As such, the overturned fasteners 7 could be more reliably and steadily placed on the rotational plate 2.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An automated testing device for fasteners, comprising:
    a platform;
    a rotational plate on a top side of said platform; and
    an uploading member, a guiding member, an optical testing member, and an unloading member, sequentially positioned around said rotational plate along a rotational direction of said rotational plate;
    wherein said rotational plate is a circular plate made of a metallic material or transparent glass;
    said uploading member comprises a rail where fasteners to be tested are placed and delivered sequentially in an upright manner to said top side of said rotational plate;
    said guiding member comprises a shut element having a curved surface above said rotational plate to align said fasteners to be tested along a specific path;
    said optical testing member comprises at least an image capturing element for obtaining and examining at least a profile image for each fastener to be tested on said path;
    an unloading member comprises a first unloader and a second unloader positioned sequentially along said rotational direction of said rotational plate which drive substandard and qualified fasteners out of said rotational plate, respectively;

said uploading member further comprises an overturning element between an output end of said rail and said top side of said rotational plate; said overturning element comprises a wheel set and a matched horseshoe-like piece; said wheel set comprises an inner wheel and an outer wheel in parallel so that a body section of each fastener to be tested is held between said inner and outer wheel; and a curved passageway between said piece and said wheel set is provided so that a cap section of each fastener to be tested moves along said passageway.

2. The automated testing device according to claim 1, wherein said guiding member is one of a fixed curved wall and a motor-driven wheel.

3. The automated testing device according to claim 1, wherein said optical testing member comprises a lateral image capturing element outside said rotational plate viewing in a centripetal direction, a perpendicular image capturing element above or beneath said rotational plate, and one of a programmable logic controller and a computational processing unit for examining fasteners images obtained by said image capturing elements.

4. The automated testing device according to claim 3, wherein said first unloader is selectively engaged by said programmable logic controller or said computational processing unit to provide an airflow to drive substandard fasteners out of said rotational plate; and said second unloader provides a curved wall so that qualified fasteners are moved along said curved wall and fall out of said rotational plate.

5. The automated testing device according to claim 1, wherein said optical testing member further comprises a sensor so as to trigger an image taking action of said image capturing element when a fastener to be tested is sensed by said sensor.

6. The automated testing device according to claim 1, wherein at least said outer wheel is driven by a motor; and, if only said outer wheel is driven by a motor, said inner wheel has a back segment removed so as to form a vertical chord adjacent to the center of said inner wheel.

* * * * *